United States Patent
Vain et al.

(10) Patent No.: US 9,808,183 B2
(45) Date of Patent: Nov. 7, 2017

(54) DEVICE AND METHOD FOR REAL-TIME MEASUREMENT OF PARAMETERS OF MECHANICAL STRESS STATE AND BIOMECHANICAL PROPERTIES OF SOFT BIOLOGICAL TISSUE

(75) Inventors: Arved Vain, Tartu (EE); Aleko Peipsi, Tallinn (EE); Mart Liik, Tallinn (EE)

(73) Assignee: MYOTON AS, Tallinn (EE)

( * ) Notice: Subject to any disclaimer, the term of this patent is extended or adjusted under 35 U.S.C. 154(b) by 1164 days.

(21) Appl. No.: 13/977,873

(22) PCT Filed: Jul. 7, 2011

(86) PCT No.: PCT/EE2011/000009
§ 371 (c)(1),
(2), (4) Date: Jul. 1, 2013

(87) PCT Pub. No.: WO2012/089221
PCT Pub. Date: Jul. 5, 2012

(65) Prior Publication Data
US 2013/0289365 A1     Oct. 31, 2013

(30) Foreign Application Priority Data
Dec. 31, 2010  (EE) .................................. 201000094

(51) Int. Cl.
*A61B 5/00*  (2006.01)
*A61B 5/103*  (2006.01)
(Continued)

(52) U.S. Cl.
CPC ............ *A61B 5/103* (2013.01); *A61B 5/0051* (2013.01); *A61B 5/0053* (2013.01);
(Continued)

(58) Field of Classification Search
CPC ......... A61B 9/00; A61B 5/103; A61B 5/0053; A61B 5/4519; A61B 90/06;
(Continued)

(56) References Cited

U.S. PATENT DOCUMENTS 3,022,400 A  *  2/1962  Von Ahlefeldt ...... H01F 7/1615
                                                335/255
4,177,798 A     12/1979  Gras et al.
(Continued)

FOREIGN PATENT DOCUMENTS

DE    4343612 A1    6/1995
RU    2326583 C1    6/2008
(Continued)

OTHER PUBLICATIONS

International Search Report for International Application No. PCT/EE2011/000009, dated Nov. 7, 2011.
(Continued)

*Primary Examiner* — Timothy J Neal
*Assistant Examiner* — Aaron B Fairchild
(74) *Attorney, Agent, or Firm* — Heslin Rothenberg Farley & Mesiti P.C.; Victor A. Cardona, Esq.

(57) ABSTRACT

A device and a method for simultaneous recording, in real time, parameters characterising the mechanical tension, elasticity, dynamical stiffness, creepability and mechanical stress of soft biological tissue are provided. By means of the myometer, a constant external pre-pressure is created, independently of the device's position, between the tissue and the testing end of the device. Next, the tissue is subjected to a short-term external dynamic influence. A mechanical change in the shape of the tissue and its mechanical response are registered as a graph of the tissue's oscillations. For calculating the parameters, a time span on the graph is used which involves an oscillation period from the beginning to
(Continued)

the end of the effect on the tissue plus its subsequent first 1.5 self-oscillation period. This enables recording and data-processing to be carried out simultaneously as well as statistically significant estimates to be made in real time.

10 Claims, 2 Drawing Sheets

(51) Int. Cl.
  *A61B 9/00*   (2006.01)
  *H01F 7/122*   (2006.01)
  *H01F 7/16*   (2006.01)
  *G01D 5/20*   (2006.01)

(52) U.S. Cl.
  CPC .............. *A61B 5/4519* (2013.01); *A61B 9/00* (2013.01); *G01D 5/2033* (2013.01); *H01F 7/122* (2013.01); *H01F 7/1615* (2013.01)

(58) Field of Classification Search
  CPC ........ A61B 2090/064; A61B 2090/065; A61B 5/44; A61B 5/441; A61B 5/45; G01D 5/2033; H01F 7/122; H01F 7/1615
  USPC .................... 600/587, 592, 552; 73/574, 576
  See application file for complete search history.

(56) References Cited

U.S. PATENT DOCUMENTS

| | | | | |
|---|---|---|---|---|
| 5,154,085 A | * | 10/1992 | Takeda | ..................... G01N 3/38 374/47 |
| 5,766,137 A | * | 6/1998 | Omata | ............... A61B 5/02007 600/587 |
| 6,132,385 A | | 10/2000 | Vain | |
| 2009/0056427 A1 | | 3/2009 | Hansma et al. | |

FOREIGN PATENT DOCUMENTS

| | | |
|---|---|---|
| WO | 9116003 A1 | 10/1991 |
| WO | 2008/081276 A1 | 7/2008 |
| WO | 2011007023 A2 | 1/2011 |

OTHER PUBLICATIONS

Preliminary Search Report issued by the Estonian Patent Office dated Feb. 28, 2012 regarding Application No. P201000094.
Examination Report issued by the European Patent Office dated May 26, 2014 regarding PCT/EE2011/000009 filed on Jul. 7, 2011.

* cited by examiner

DEVICE AND METHOD FOR REAL-TIME MEASUREMENT OF PARAMETERS OF MECHANICAL STRESS STATE AND BIOMECHANICAL PROPERTIES OF SOFT BIOLOGICAL TISSUE

CROSS REFERENCE TO RELATED APPLICATIONS

This application is a national stage filing under section 371 of International Application No. PCT/EE2011/000009, filed on Jul. 7, 2011, and published in English on Jul, 5, 2012 as WO 2012/089221 and claims priority of Estonia Patent Application No. P201000094, filed on Dec. 31, 2010, the entire disclosures of which are incorporated herein by reference.

FIELD OF THE INVENTION

This invention belongs to the realm of medical technology, it is designed to measure the mechanical stress and biomechanical properties of the parameters of soft biological tissues and to statistically assess their state in real time.

BACKGROUND OF THE INVENTION

The biomechanical properties of soft biological tissue involve its elasticity, dynamical stiffness, creepability, and mechanical stress relaxation time.

In evidence-based medicine, both the parameters characterising the stress of superficial soft biological tissues, for example of skeletal muscle, and its biomechanical properties are used as a supplementary source of information. The said parameters allow specialists to quantitatively determine the extent of pathological processes, and the efficiency of various massage techniques, physiotherapeutic procedures, medication and training programmes, as well as ascertaining the tone of tissues during an operation, and fixing the time of death in forensics.

Until now, many attempts have been made to measure the stress (tone) of soft biological tissues by various methods, but neither has such a device been invented nor such a method found yet that would measure all the variables characterising the abovementioned parameters in a way that is universal and realisable/applicable in daily clinical practice in real time.

Tone is defined as the mechanical stress of skeletal muscle with no voluntary contraction of the muscle. If we multiply the numerical value of the skeletal muscle stress by its cross-section area, we get the value of the force by which the tendon of skeletal muscle is pulling the periosteum of the bone.

There are three types of tone:
1) The passive resting tone—a state of skeletal muscle with no contraction in the muscle when the muscle is not balancing force torques on the observed joint axis caused by the force of gravity with its mechanical tension. There is no electomyographic (EMG) signal.
2) The resting tone (relaxation) —a state of mechanical stress (or tension) of skeletal muscle without voluntary contraction with EMG activity due to, for instance, an emotional or pathological condition. Such a state is more variable than the passive resting tone. The muscle force torques in antagonist muscles are balanced.
3) The postural tone is a state of skeletal muscle in which the muscle is balancing the force torques of body segments caused by the force of gravity in order to maintain the equilibrium position. When keeping the position, the muscle tension and stiffness are changing persistently, the variability of which is several times greater than in passive relaxed tone. The state of mechanical tension and stiffness level are also significantly higher.

The tone of the skeletal muscle cannot be decreased at will. The level of the tone depends on intramuscular pressure—the higher the intramuscular pressure, the greater the mechanical tensile stress in the muscle (Vain A. 2006 The Phenomenon of Mechanical Stress Transmission in Skeletal Muscles. Acta Academiae Olympiquae Estoniae, Vol 14, No. 1/2 pp. 38-48). If the intramuscular pressure is high, the outflow of venous blood from the muscle will slow down because the veins have no substantial internal blood pressure and when the intramuscle pressure rises, then the veins' cross-section area will decrease. In the case of passive rest, this causes the situation that skeletal muscles' ability to work is restored slowly. Additionally, the ergonomic efficiency of muscle activity in performing movements will decrease since the moment of force caused by antagonist muscles for turning the part of the body on the axis of the joint increases on account of the work needed to stretch the antagonist muscles. The amount of work A done when stretching the antagonist muscles can be calculated by the following formula:

$$A = F_{resistance} * s (J)$$

where $F_{resistance}$—resistant force (N), s—extent of stretch (m), whereas $$F_{resistance} = 2*v*f*D*m (N),$$

where
v—speed of stretching (m/s),
f—muscle's natural oscillation frequency (Hz),
D—logarithmic decrement of a muscle's natural oscillation,
m—mass of the muscle being stretched (kg).

It is technically complicated to measure skeletal muscle's state of mechanical stress. However, there has been revealed a functional connection between a material's natural oscillation frequency and its mechanical stress, which in the case of short-term measurements makes it possible to characterise the mechanical state of skeletal muscle.

The logarithmic decrement of a muscle's natural oscillation shows how much mechanical energy dissipates during one period of the muscle's natural oscillation. Hence, the elasticity of skeletal muscle (one of the biomechanical qualities of the muscle) can be characterised via the logarithmic decrement of the muscle's natural oscillation. Elasticity of soft biological tissue means its ability to restore its former shape after the deforming force is removed. The opposite term to elasticity is plasticity. If an elastic body changes its shape as a result of an impulse transmitted by external forces, then simultaneously mechanical energy of elasticity is stored in the morphological structures of skeletal muscle which possess elasticity properties. When the impulse from the deforming force ends, then the stored mechanical energy will restore the body's initial shape at a velocity that accords to the value of the logarithmic decrement—very quickly if the value approaches zero, and more slowly if the value is higher. Hence, in a device built to register the parameter characterising elasticity, the effect of oscillation damping must be brought to a minimum.

In a working muscle, contraction and relaxation alternate. The duration of each may vary. Sometimes it may last only a split of a second. If the relaxation period is short and the muscle's logarithmic decrement is big, then the initial shape of skeletal muscle fails to be completely restored, the muscle's internal pressure falls insufficiently and, as a result, the outflow of venous blood from the muscle is slowed down. The time taken for the muscle's work capacity to be restored increases, its fatigue also increases, and the danger of a muscle overload trauma becomes a reality.

Stiffness is a biomechanical property of skeletal muscle which consists in its resistance to any force changing its shape. The property inversely proportional to stiffness is compliance. The unit of measurement of stiffness is N/m. How economical and how accurately co-ordinated a person's movements are depends on the stiffness of his/her skeletal muscles. Creepability is a biomechanical property of soft biological tissue to deform permanently under constant stress. The creepability property of liquids has been quantitatively measured (U.S. Pat. No. 4,534,211, Molina O. G. 1985).

The creepability property of soft biological tissue might be characterised, for example, by the Deborah number De. The Deborah number is a quantity whose dimension is 1; this number is used to characterise the viscoelasticity of tissues (or creepability of materials). The latter is expressed as the ratio of relaxation time, $t_{material}$ representing the intrinsic properties of tissue, and the characteristic time scale of an experiment, or deformation time, tprocess:

$$D_e = \frac{t_{material}}{t_{process}}.$$

The relaxation property of skeletal muscle tissue is defined as the tissue's ability to relieve itself of mechanical stress in the case of constant length.

The viscoelastic properties of skeletal muscle tissue are characterised by creepability and relaxation (Fung Y. C. 1981 Biomechanics. Mechanical Properties of Living Tissues p. 41).

Various attempts have been made to measure the state of mechanical stress and biomechanical properties of soft biological tissues in vivo. As a result, humanity knows a host of instruments for measuring mechanical stress and stiffness, but no ways have been invented as yet to express creepability and relaxation time of mechanical stress in numerical terms. No such devices or methods are known that would simultaneously measure muscle tone and all the four abovementioned biomechanical properties in real time.

The principal problem is how to evaluate the state of a person's skeletal muscles on the basis of measurement data, while the parameters characterising this state are constantly changing due to their involvement in biological processes. Therefore, it is insufficient to represent the state of soft biological tissue by one parameter only, which reflects the level of measurable quantities; considering the aspect of diagnostic information, it is relevant that a characteristic describing the variation of levels be added. For assessment of variation, it is important that the reading of the measuring device be repeated in short-term measuring scales (e.g. measuring after every 1 second). In this case, measuring should be carried out and monitored by measuring software (firmware), in order to collect in a short term a sufficient amount of measurement data for statistical assessment. No such methods of measurement are known as yet in the diagnostics of soft biological tissues.

Indeed, both methods and devices are available for numerical characterisation of biological tissues' viscoelasticity (e.g., WO2007144520 Method of measuring Viscoelastic Properties of Biological Tissue Employing an Ultrasonic Transducer, EchoSens S.A., 2006), but neither methods nor devices have been disclosed to date that would separately characterise creepability and relaxation properties of soft biological tissues.

None of the earlier solutions allow measurement to be repeated in a short term because the impact on soft biological tissue tends to change the measurable quantities, the character of the measurements is not standardised, and the impact does not end with a quick release.

Among the known solutions, the method closest to the present invention is the myometer, a device and method for recording of mechanical oscillations in soft biological tissues (EE03374B1, Vain A. 2001). The essence of the myometer lies in causing a short-term effect on soft biological tissue by giving it a mechanical impulse and subsequently recording the tissue's mechanical response by means of an electromechanical sensor (acceleration sensor).

One drawback of this solution of the closest prior art is that while the obtained acceleration graph enables calculation of the tissue's natural oscillation frequency, indicating its state of stress as well as the logarithmic decrement characterising its elasticity and dynamic stiffness, it does not make it possible to determine the parameters describing creepability and relaxation time of mechanical stress. Secondly, the parameters characterising the tissue's state of mechanical stress, elasticity and stiffness are calculated at different moments of the oscillation, which yields varying results since the mass participating in the oscillation process decreases constantly due to dissipation of mechanical energy in the case of damped oscillation.

Resulting from the construction of said device (inclusion of a lever), the impulse may be followed by resonant oscillations of the parts exerting impact. If the size of the device is reduced, then the shoulder of the lever will become so short that it will cause a 'scraping' impact, which may yield incorrect results as the direction of the tissue's deformation changes during stimulation. Another shortcoming is the constructional solution of the above prior art device, in which bending of the signal cable attached to the acceleration sensor during oscillation will bring about dissipation of the energy of impact.

A shortcoming of the cited prior art device is also the feature that the construction of the measuring apparatus involves rotating details, which need fine tuning to minimise resistance caused by mechanical friction. But the greater the resistance, the less sensitive the device.

An additional drawback of the said closest prior art device is that in such cases when the direction of the testing end with respect to the Earth's gravitational field is changed, the pre-pressure exerted by the mass of the testing end on the superficial tissues covering the muscle will decrease. However, preservation of constant pre-pressure is necessary for delivering the impact energy to the muscle and thereby making it oscillate. If the pre-pressure decreases, the role of superficial tissues grows both in recording the muscle's natural oscillation frequency and in the resulting measurements.

Thus, there exists a need for such a device and method that would allow us to measure in real time, simultaneously, quickly and accurately soft biological tissue's mechanical state of stress and parameters characterising its four biomechanical properties: elasticity, dynamic stiffness, creepability and mechanical stress relaxation time, and achieve, irrespectively of the position of the device in the gravitation field, high sensivity of the device as well as repeatability and reliability of the results.

DISCLOSURE OF THE INVENTION

The aim of the present invention is to provide a universal device and method for simultaneous measuring, in real time, of parameters characterising the state of mechanical stress, elasticity, dynamic stiffness, creepability and mechanical stress relaxation time of soft biological tissues.

To achieve this aim, a device (myometer) comprises the body (1), the processor and controller for governing the measuring process and for calculating parameters (a control means) (2), a recorder, e.g. acceleration sensor (3), the testing end (4), the drive, of the testing end position sensors (6, 7) of a moving frame (9), and a shutter (8) of the said position sensors, whereas the drive of the testing end is operable in translational motion, without mechanical friction, and is having the same direction as the testing end, and where in the drive of the testing end comprises a testing end mechanism including a moving frame (9) and elastic elements, e.g. elastic plates (10 and 11), whose one ends are inflexibly fastened by collet-type coupling (12) to the base (13), and the other ends are inflexibly fastened by collet-type coupling (12) to a moving frame (9) and whereas the centre of the moving frame (9) surrounds a sleeve (14) which is containing permanent magnets (15, 16) oriented with poles of the same name facing each other and placed in the centre of a solenoid (5), and a testing end (4) whose electrical-steel (i.e. remagnence-free (free of residual magnetism)) cone-shaped end (17), fixed vis-à-vis the directing inflexible moving frame (9), is located in the pulling zone of one of the permanent magnets within the moving frame (9), and said device is equipped with a friction-free element, e.g. a flexible flat cable (18) for direction of the recorder's (3) signal from the moving frame (9) to the control means (2), and the device involves light and/or sound signals placed around an aperture (19) in the testing end (4), and an arresting system involving a drive (20), an actuating screw (21), a slider (22) moving on unmoving base (13) and having a shutter (23), and a means (24) for avoiding mechanical damage to the arresting system, and stoppers (25, 26) of the moving frame together with position sensors (27, 28 and 29). The device is operated by a computer program product stored in the processor memory and comprising portions of the software code adapted to perform the method by stages when the program is running in the processor.

The device's construction and software (computer program) enable the user to achieve repeatability and reliability of the measuring results, allowing simultaneous measurement of the parameters and processing of data as well as making statistically significant judgements in real time.

The technical solution of the construction elements of the current invention makes it easy to assemble the device. Nor will the device need any fine tuning once it has been assembled. There is no need for tuning joints, e.g. the measuring mechanism.

The method for simultaneous measurement of the parameters characterising the biological tissue's state of mechanical pressure, elasticity, dynamic stiffness, creepability and mechanical stress relaxation time involves the following stages:

Stage A 1) a means for marking the area to be investigated and for facilitating the contact between the testing end and tissue without damaging the latter's integrity and function is attached either to the testing end or the surface of the tissue;

2) the device disclosed above (myometer) is moved close to the surface being measured, in the course of which, irrespectively of the positioning of the device, the gravitation field and the user, the device causes between the tissue under investigation and the testing end a constant external influence (pre-pressure) with force equalling the weight of the testing end mechanism. The pre-pressure is maintained in stages B-D throughout the series of measurement;

3) the placing of the device is stopped when either the light or sound signal of the device changes, indicating that the necessary pre-pressure has been achieved and the elastic element is stress-free, i.e. the preconditions for starting a series of measurements have been met;

Stage B

The device described above exerts on soft biological tissue an external single impact for a prescribed number of times by a single impulse of the solenoid's constant electrical power, each impact ends with a quick release. At the start of the impact, the elastic element is stress-free. Throughout the series of measurements, during the prescribed time, the device is kept in the same position until a change of either the light or sound signal indicates the end of the series.

The parameters of a single external mechanical impulse are chosen, depending on the aims of the diagnostic information, from the following ranges: specific power from the range 0.01-0.2 W/mm2, the quick release from the range 0.1-15 ms, and the time for achieving the maximum impulse from the range 1-5 ms.

Stage C

The mechanical change in the tissue's shape and the tissue's subsequent mechanical response are recorded, in real time, as graphs of the tissue's natural oscillations, for instance, as graphs of acceleration following each impulse in stage B.

Stage D

In addition to calculating the state of mechanical stress, elasticity and dynamic stiffness, simultaneously the parameters characterising the tissue's creepability and relaxation time of mechanical stress together with statistical assessment of all the calculated parameters are computed in real time; for calculating the parameters characterising soft biological tissue's state of mechanical stress, elasticity, dynamic stiffness, creepability and relaxation time of mechanical stress, the time range from the measured tissue's natural oscillations graph is used, for instance, the time range shown by the accelerations graph, which involves the period from the start to the end of the impact and 1.5 oscillation periods of the tissue's subsequent natural oscillations.

The measuring series consists of single measurements in which the first measurement starts with stage A and is followed by stages B, C, and D. The next measurement in the series proceeds with repetition of stages B, C, and D until completion of the prescribed number of measurements.

To perform stages A to D and calculate the parameters, specially designed software (firmware) is used, which has been stored in the device's processor, comprises portions of software code, and has been adapted to perform stages A to D when the device's firmware is used in the processor. Measuring will be repeated in minimum 1-second intervals for as many times as required for statistical assessment.

By means of the device's firmware, preliminary processing will then be carried out for statistical assessment; the information obtained will enable us to give reliable answers within a few seconds after the end of the measurement, and the repeatability and reliability of the results will be sufficiently accurate to assess both the current state of the soft biological tissue and the longitudinal trends. The above device and method for measuring soft biological tissue's state of mechanical stress and parameters of biomechanical properties allow monitoring the object under investigation in the event of different body postures and various levels of gravitation fields, as well as doing it repeatedly, autonomously, portatively, and in a non-disturbing, non-invasive and cost-effective way (cheaply).

DESCRIPTION OF THE EMBODIMENTS

Figure 1:
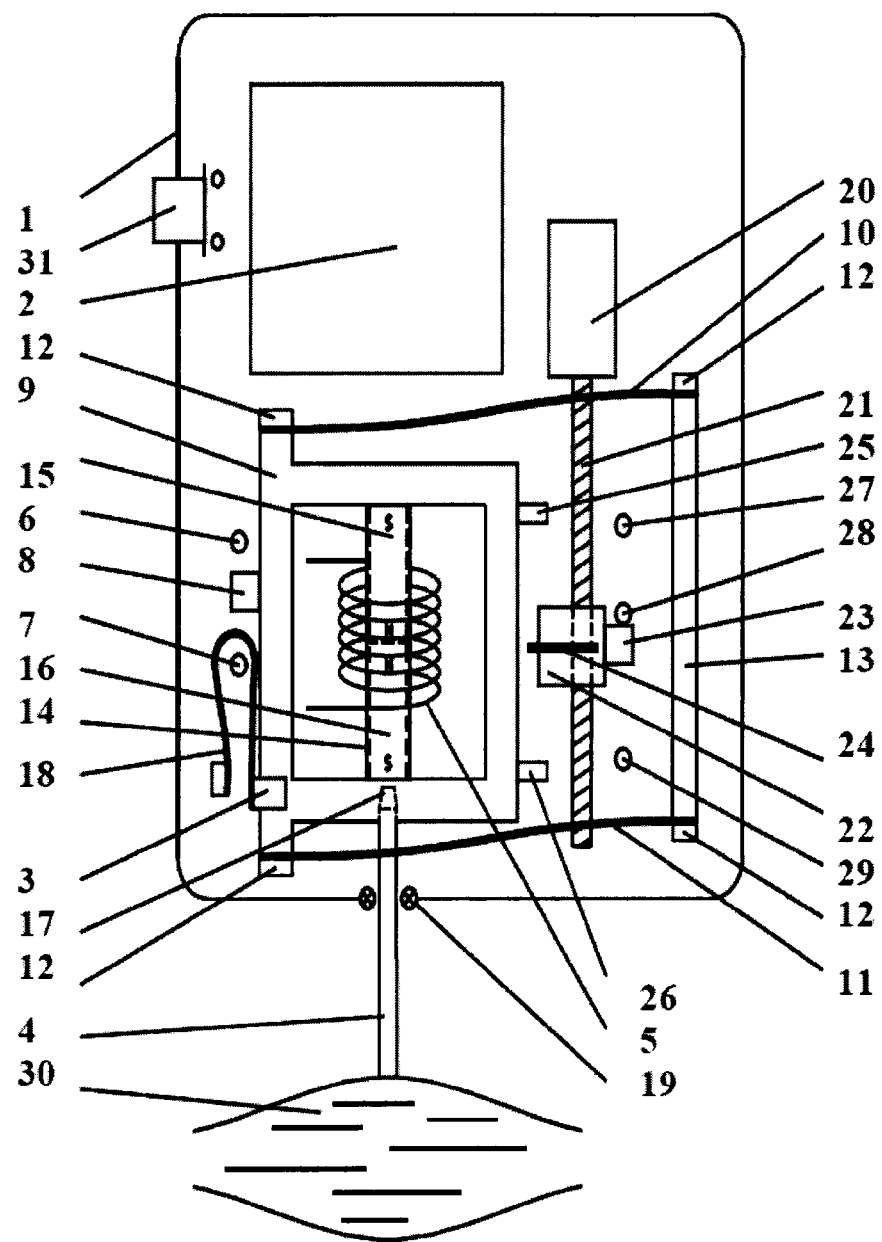
FIG. 1 Principal schematic representation of the device.

The device for recording the state of mechanical stress and biomechanical properties of soft biological tissues (FIG. 1) comprises the body 1, with a means at its top holding a processor and controller for monitoring the measuring process and for calculating the parameters (a control means 2), a recorder 3 and a moving frame 9 fastened to an inflexible base 13 by an elastic element, such as elastic plates 10 and 11. The moving frame 9 incorporates a sleeve 14 containing two permanent magnets 15 and 16, whose same-name poles are oriented face to face, while the testing end 4 has been attached to the permanent magnet 16 by means of a cone-shaped end 17 made of either electrical steel or some other suitable material. To the bottom part of the moving frame 9, a acceleration sensor 3 has been inflexibly fastened and to the middle of the frame, a shutter 8.

Above and beneath the shutter 8, the position sensors 6 and 7, respectively, have been inflexibly fastened to the body 1. In the upper and lower parts of the moving frame 9 are located inflexibly fastened stoppers 25 and 26.

The arresting system of the moving frame 9 comprises a drive 20, an actuating screw 21, a slider 22 with a shutter 23 and a means 24 for preventing mechanical damage to the arresting system. Along the axis of movement of the arresting system are placed position sensors 27 (upper), 28 (middle) and 29 (lower), which are inflexibly connected with the body 1.

A solenoid 5 has been inflexibly fastened to the body 1, lying in the middle of the moving frame 9.

When the measuring process is triggered by turn of the switch 31, the solenoid 5 is activated by electric current directed by the signal picked up from the axis of the acceleration sensor 3, depending on how the body 1 is oriented in the gravitation field. Constant current in the solenoid 5 gives rise to a constant force affecting the two permanent magnets 15 and 16 located in its magnetic field, as a result of which constant pressure is exerted on the slider 22 by the stopper 25 of the moving frame 9. (This pressure is subsequently conveyed by the testing end 4 to the biological tissue being measured.) Subsequently, the position sensors 6 and 7 of the moving frame 9 are activated, and the slider 22 is positioned by means of the drive 20 and actuating screw 21 from the topmost to the middle position determined by the position sensor 28. As a result, the shutter 8 of the moving frame 9 will expose the light beam proceeding from the position sensor 6 (in the measuring position vis-à-vis the body 1), and cover the light beam proceeding from the position sensor 7 (vis-à-vis the body 1); the testing end 4 will emerge from the opening in the body and the signal lights surrounding the aperture 19 in the testing end will be switched on. Starting from this moment, the device is ready to perform measurements.

Figure 2:
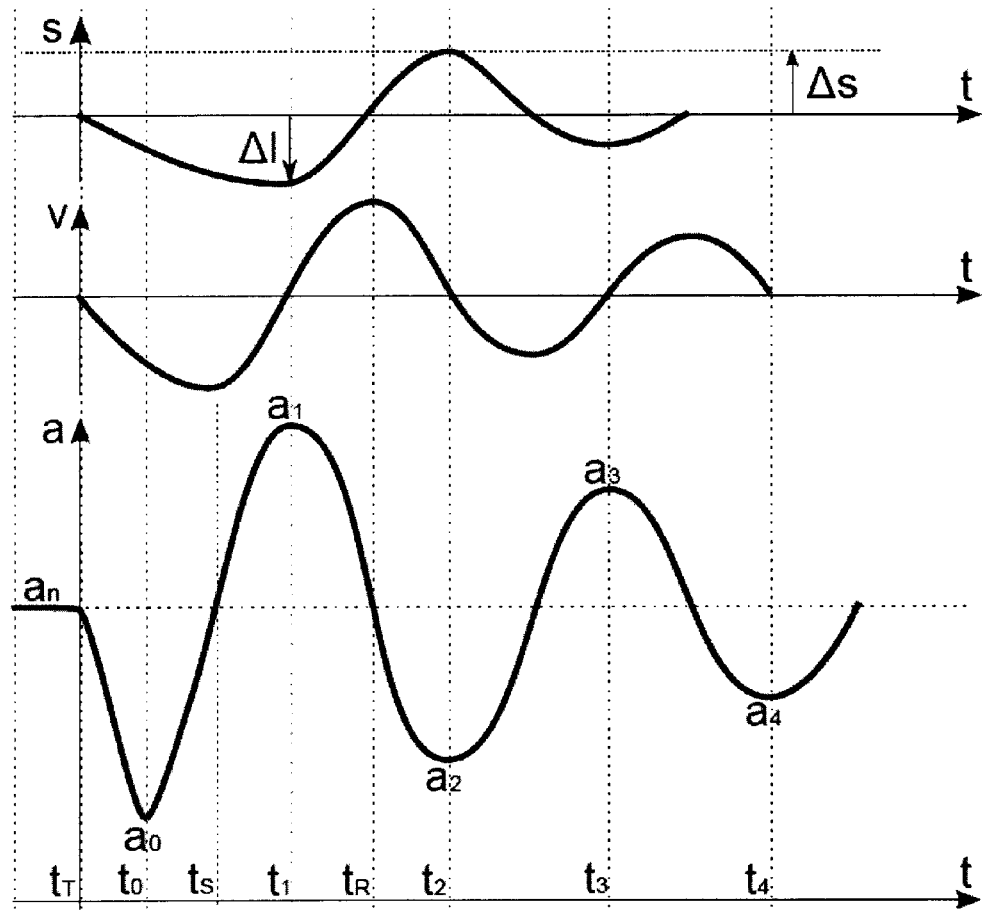
FIG. 2 Graph of soft biological tissue's natural oscillation, where
$t_T$—instant at which the drive of the testing end starts impacting the soft biological tissue mechanically;
$t_S$—the drive of the testing end is switched off;
$t_1$—the beginning of the mechanical influence of the soft biological tissue on the testing end;
$t_2$—the end of the restoration of its former shape by the soft biological tissue;
$t_1$-$t_T$—duration of the mechanical impact on the soft biological tissue;
$t_R$-$t_1$—time taken by the soft biological tissue to restore its former shape after deformation;
$a_1$-maximum acceleration of deformation of the soft biological tissue;
$t_4$-$t_1$—1.5 natural oscillation periods;
a—graph of the acceleration of the testing end;
v—graph of the velocity of the testing end;
s—graph of the trajectory of the testing end.

The method applied when using the device comprises the following. To carry out measurement, the testing end 4 is placed on the tissue 30 under investigation, causing a deformation ΔS (FIG. 2). Next, the body 1 of the device is moved towards the tissue until the discontinued beam of light from the position sensor 7 (in the measuring position vis-à-vis the body 1) is exposed by the shutter 8, whereas the shutter 8 has not yet covered the light beam proceeding from the sensor 6 (in the measuring position). In the position when the shutter 8 is between the position sensors 6 and 7 and has not yet covered their beam of light, the colour of the light proceeding from the aperture 19 changes, indicating the position of the moving frame 9 in which the elastic plates 10 and 11 are stress-free. Subsequently, impulses of current with a fixed shape, duration and frequency are transmitted to the solenoid 5.

Following each impulse, the soft biological tissue undergoes a dynamic transformation Δl (FIG. 2), which ends with a quick release, after which the biological tissue 30, in accordance with its elasticity properties, undergoes a series of free damping co-oscillations along with the testing end 4, the moving frame 9, and the recorder 3. The tissue's natural oscillation is registered by the recorder 3, and the processor will calculate, in real time, the parameters characterising the tissue's mechanical stress and biomechanical properties, as well as the criteria required for assessment.

If during the measuring session the device leaves the space between the sensors 6 and 7 marking the measuring position of the moving frame 9, or if one of the named position sensors' beams is discontinued by the shutter 8, then the control means 2 of the device will stop the measuring process and the colour of the light will change. The initial colour of the light source will not be restored, unless the position of the moving frame 9 with respect to the sensors 6 and 7 of the measuring position is restored and the measuring session can resume from where it stopped.

After the measuring session has been completed, the arresting system will fix the moving frame 9 in its upper limiting position.

By means of the above device and method the parameters of the biomechanical properties of the state of mechanical stress—elasticity, dynamic stiffness, creepability and mechanical stress relaxation time—were measured in the Biceps brachii, Flexor c.rad., Extensor digitorum muscles and Tendo calcanei simultaneously in real time, after which the data were processed and statistical assessment made.

The named procedures were performed as follows:

Stage A
1) To the testing end of the device (myometer) described above a marker was fastened for marking the area chosen for measurement and for connecting the testing end with the muscle being measured without changing the integrity and function of the biological tissue, i.e., without damaging the tissue, and the testing end was then placed on the surface of the soft tissue to be measured;
2) the device indicated in item 1) was then brought close to the surface being measured until the device's light or sound signal changed;
3) next, irrespective of the position of the device vis-à-vis the gravitation field, an external influence was exerted on the tissue by the testing end by a force equalling the weight of the testing end mechanism; thus, a static deformation $\Delta S$ of the tissue was brought about (FIG. 2);
4) the device was held in the same position (for a prescribed time period) until the light or sound signal changed.

Stage B
An external impact was exerted on soft biological tissue by a single constant electrical impulse of the solenoid, which ended with a quick release, while the elastic element of the device was stress-free. The specific power of the impulse was 0.1 W/mm$^2$, the quick release lasted 0.1 ms, and the maximum of the impulse was achieved in 3 ms. As a result, the dynamic transformation $\Delta l$ was caused on the tissue (FIG. 2).

Stage C
The mechanical transformation of the tissue was recorded together with the tissue's subsequent mechanical response in the form of a acceleration graph of the tissue's natural oscillation. The recordings were performed a certain prescribed number of times within intervals less than 1 sec (FIG. 2).

Stage D
On the basis of the acceleration graph of the tissue's natural oscillation, in real time and simultaneously, the parameters of the measured tissue's mechanical stress, elasticity, dynamic stiffness and mechanical stress relaxation time were calculated, using the time span on the natural oscillations acceleration graph which consisted of the oscillation period starting with the impact and lasting until its end plus subsequent 1.5 periods of the tissue's first natural oscillation.

The natural oscillation diagram, results of measurement and the orientation of the device were stored by means of a computer program in the memory of the device.

The repeated measurements were carried out after min. 1-second intervals for a sufficient number of times for making statistical estimations. The results were displayed on the LCD screen of the recorder.

The acceleration curve obtained by measurements made by the device (myometer) described above (FIG. 2) enabled calculation of the natural oscillation f of the oscillating muscle mass (together with the mass of the testing end), which is expressed as the inverse value of the oscillation period T $$f_1/T \; [Hz],$$

$$\text{dynamic stiffness } C = m_t * a_1 / \Delta l \; [N/m],$$

where $m_t$—is the mass of the moving part in kg,
  $a_1$—acceleration at the time when the testing end is dug deepest in the tissue—m/s$^2$,
logarithmic decrement $$\Theta_1 = ln(a_1/a_3).$$

Also, it became possible to calculate, in the myometric method described above, the relaxation time $t_{rel}$ of the tissue, which is expressed by the formula $$t_{rel} = t_2 - t_1.$$

The Deborah number characterising the creepability of the tissue was calculated by the following formula:

$$D_e = \frac{t_2 - t_1}{t_1 - t_T}$$

The results of the measurement are given in Table 1 below.

TABLE 1

Measurements of the muscle tone and biomechanical properties of a 24-year-old male athlete at rest.

| Object | Side of body | Statistics | Frequency Hz | Decrement | Dynamic stiffness N/m | Creepability | Relaxation time ms |
|---|---|---|---|---|---|---|---|
| Biceps brahii | Right | Average | 13.15 | 1.17 | 192 | 1.36 | 22.65 |
| | | Median | 13.14 | 1.18 | 193 | 1.36 | 22.50 |
| | | St-deviation | 0.23 | 0.04 | 7.9 | 0.06 | 0.97 |
| | | Var. coeff % | 1.76 | 3.60 | 4.1 | 4.36 | 4.27 |
| | Left | Average | 12.93 | 1.13 | 180 | 1.33 | 22.28 |
| | | Median | 12.99 | 1.13 | 180 | 1.33 | 22.20 |
| | | St-deviation | 0.17 | 0.02 | 4.0 | 0.04 | 0.39 |
| | | Var. coeff % | 1.32 | 2.16 | 2.2 | 2.73 | 1.74 |
| Student t-test (<5%) | | | YES | YES | YES | YES | NO |
| Extensor digitorum | Right | Average | 15.22 | 0.81 | 216 | 1.01 | 16.94 |
| | | Median | 15.28 | 0.79 | 218 | 1.01 | 16.90 |
| | | St-deviation | 0.30 | 0.05 | 12.7 | 0.04 | 0.53 |
| | | Var. coeff % | 1.98 | 5.87 | 5.9 | 4.09 | 3.11 |
| | Left | Average | 14.24 | 0.97 | 192 | 1.17 | 19.48 |
| | | Median | 14.29 | 0.97 | 195 | 1.20 | 19.70 |
| | | St-deviation | 0.22 | 0.02 | 8.5 | 0.07 | 0.74 |
| | | Var. coeff % | 1.57 | 2.38 | 4.4 | 6.37 | 3.82 |

TABLE 1-continued

Measurements of the muscle tone and biomechanical properties of a 24-year-old male athlete at rest.

| Object | Side of body | Statistics | Frequency Hz | Decrement | Dynamic stiffness N/m | Creepability | Relaxation time ms |
|---|---|---|---|---|---|---|---|
| Student t-test (<5%) | | | YES | YES | YES | YES | YES |
| Flexor carpi radialis | Right | Average | 15.66 | 1.35 | 247 | 1.05 | 16.84 |
| | | Median | 15.69 | 1.35 | 247 | 1.06 | 16.90 |
| | | St-deviation | 0.13 | 0.03 | 6.1 | 0.03 | 0.27 |
| | | Var. coeff % | 0.83 | 2.12 | 2.5 | 2.43 | 1.59 |
| | Left | Average | 15.80 | 1.30 | 253 | 0.97 | 15.65 |
| | | Median | 15.80 | 1.29 | 253 | 0.96 | 15.60 |
| | | St-deviation | 0.29 | 0.06 | 9.9 | 0.04 | 0.53 |
| | | Var. coeff % | 1.83 | 4.58 | 3.9 | 3.87 | 3.40 |
| Student t-test (<5%) | | | NO | YES | YES | YES | YES |
| Tendo calcanei | Right | Average | 30.32 | 1.11 | 605 | 0.44 | 6.50 |
| | | Median | 30.77 | 1.18 | 607 | 0.45 | 6.60 |
| | | St-deviation | 0.96 | 0.13 | 12.1 | 0.01 | 0.15 |
| | | Var. coeff % | 3.15 | 11.24 | 2.0 | 2.42 | 2.26 |
| | Left | Average | 35.09 | 1.04 | 672 | 0.38 | 5.59 |
| | | Median | 35.16 | 1.03 | 671 | 0.38 | 5.60 |
| | | St-deviation | 0.41 | 0.02 | 12.6 | 0.01 | 0.15 |
| | | Var. coeff % | 1.17 | 1.93 | 1.9 | 3.52 | 2.74 |
| Student t-test (<5%) | | | YES | YES | YES | YES | YES |

Due to the small values of standard deviation, the differences between the parameters of the right and left side of the body are statistically significant even in the case of small values, which shows the great sensitivity and accuracy of the device. The decrement characterising the elasticity of tendo calcanei of the left side of the body has 11.24% variation, calling for the need to repeat the measurement and disclose what causes the instability before appearance of pathological symptoms.

TABLE 2

Statistical indices of the measurements performed on the test body SonarAid130 by the device of the closest prior art and the device corresponding to the invention, (n = 30).

| Device | Statistical parameter | Frequency Hz | Logarithmic decrement | Dynamic stiffness N/m | Creepability | Relaxation time ms |
|---|---|---|---|---|---|---|
| Device of the closest prior art | Average | 22.12 | 0.65 | 500 | — | — |
| | Mediaan | 22.1 | 0.66 | 501 | — | — |
| | Standard dev. | 0.13 | 0.02 | 9 | — | — |
| | Var. coeff % | 0.59 | 3.07 | 1.8 | — | — |
| Device of the current invention | Average | 22.98 | 0.29 | 391 | 0.78 | 9.81 |
| | Median | 23.02 | 0.29 | 395 | 0.78 | 9.7 |
| | Standard dev. | 0.15 | 0.01 | 13.28 | 0.02 | 0.18 |
| | Var. coeff % | 0.64 | 2.72 | 3.4 | 2.78 | 1.88 |

By comparing the measurements performed on the test body by means of the prior art and the device corresponding to the current invention it appeared that the decrement was twice as small when measuring by the device corresponding to the invention, which points at the named device's substantially higher sensitivity.

Application of the device corresponding to the invention, the method and the computer program enables one to
   measure simultaneously, in real time, soft biological tissue's mechanical stress and parameters characterising its four biomechanical properties —elasticity, dynamic stiffness, creepability and mechanical stress relaxation time;
   measure and assess the state of stress and biomechanical properties of soft biological tissue with greater accuracy;
   repeat the measuring procedure within small time intervals, as the parameters for impacting on soft biological tissue by means of a single impulse are chosen so that in the course of measurements they will change neither the stress nor biomechanical properties of the tissue under investigation;
   perform measurements at different angles, maintaining the constant pre-pressure when doing so;
   measure following a prescribed algorithm;
   obtain, owing to good repeatability of measurements, within a short period of investigation, a sufficient number of measurements for statistical evaluation and/or comparison of the state of soft biological tissues with reference values;

obtain standardised criteria of assessment which are released by the firmware immediately after completion of the measurements;

raise the sensitivity of the device;

reduce the user's influence on the measurements.

The invention claimed is:

1. A device for simultaneous measurement of the parameters characterising the mechanical stress, elasticity, dynamic stiffness, creep and mechanical stress relaxation time of soft biological tissue, comprising:
    a body, a processor and controller for managing the measuring process and calculating the parameters, a testing end having a movement axis and being movable along its movement axis, a drive of the testing end comprising a movable frame and a solenoid, one end of the testing end being fixed to the movable frame, position sensors for the movable frame, and an accelerometer arranged to sense movement of the testing end,
    wherein the drive of the testing end is operable in a translational motion having the same direction as the movement axis of the testing end, the movable frame being supported by elastic plate elements so the drive of the testing end is operable with negligible mechanical friction,
    and the device also comprises light or sound signals arranged to indicate, in response to data from the position sensors, when the elastic plate elements are stress free, when an impulse of current may be transmitted to the solenoid to exert an external impact on the biological tissue; and
    wherein the controller is arranged such that in use an impulse of current is transmitted to the solenoid to exert the external impact on the biological tissue, after which the biological tissue along with the testing end, the movable frame and the accelerometer undergoes a series of damped oscillations, from which the processor is arranged to calculate the parameters characterising the biological tissue.

2. A device as claimed in claim 1, wherein the moving frame contains a sleeve with permanent magnets placed in the centre of the solenoid, the magnets being oriented with south poles face to face or oriented with north poles face to face.

3. A device as claimed in claim 2, wherein the one end of the testing end that is fixed to the movable frame includes an electrical steel cone-shaped tip that is placed in the pull zone of the permanent magnet which is located closer to the testing end, so said cone-shaped tip is fixed selfrigidly vis-à-vis the movable frame.

4. A device as claimed in claim 3, wherein said device is equipped with a friction-free element for carrying signals from the movements sensor from the movable frame to the processor and controller, the friction-free element being a flexible flat cable.

5. A device as claimed in claim 1 wherein the light signals or sounds signals are placed around an aperture in the body through which the testing end may project.

6. A device as claimed in claim 5, also comprising an arrester system comprising a drive, an actuating screw, a slider moving relative to the body, wherein the slider is equipped with a shutter, and wherein the device comprises stoppers at the extreme positions of the movable frame, together with position sensors mounted on the body.

7. A device as claimed in claim 1 wherein the elastic plates have one ends inflexibly to the movable frame and the other ends are inflexibly fastened to the body.

8. A method for simultaneous measuring, in real time, of the parameters characterising soft biological tissue's mechanical stress, elasticity, dynamic stiffness, creep and mechanical stress relaxation time, by use of a device as claimed in claim 1, comprising the following stages:
    A. on the surface of soft biological tissue under investigation a means is attached for marking an area of the soft biological tissue to be examined and for joining the testing end of the device with the biological tissue with neither damaging the latter's integrity nor changing its functions,
    B. the soft biological tissue is externally impacted by a single constant impulse of electric power from the solenoid, which ends with a quick release,
    C. the mechanical deformation of the tissue and the tissue's subsequent mechanical response are recorded in the form of a graph, e.g. an acceleration graph, of the tissue's natural oscillation,
    D. on the basis of the acceleration graph, the parameters of the tissue's mechanical stress, elasticity and dynamic stiffness are calculated,
wherein the following procedures are performed:
    in Stage A
    1) either to the testing end of the device, or to the surface of the tissue the means is attached for marking the area to be investigated and for joining the testing end with the tissue without either damaging the integrity of the tissue or changing its function, and the testing end is placed on the surface of the soft biological tissue under investigation;
    2) the device is brought near the surface being measured, in the course of which the device causes, irrespectively of its position, gravitational field and user, a constant external influence (pre-pressure) between the tissue under investigation and the testing end with force equalling the weight of the mechanism of the testing end, and the pre-pressure is maintained during the stages B-D throughout the whole series of measurements;
    3) nearing the device to the tissue is stopped when a necessary pre-pressure has been achieved and the elastic elements are stress-free, i.e. the preconditions for starting a series of measurements have been met;
    in stage B
    the device exerts an external impact on soft biological tissue for a prescribed number of times by means of a single constant electric power impulse from the solenoid, wherein each impact ends with a quick release, and the device is held in the same position throughout the measuring series until the end of the measuring series;
    in stage C
    the mechanical deformation of the tissue and subsequent mechanical response are recorded in real time in the form of a graph of the tissue's natural oscillations in stage B after each single impulse;
    in stage D
    are additionally calculated, in real time, the parameters characterising the creep and mechanical tension relaxation time together with statistical assessments of all the calculated parameters, wherein for calculating the parameters characterising the soft biological tissue's mechanical state of stress, elasticity, dynamic stiffness, creep and mechanical stress relaxation time the time span from the tissue's natural oscillations graph is used which involves the oscillation period from the start until the end of the impact and subsequent 1.5 (one and a half) periods of the tissue's natural oscillation.

9. The method according to claim 8, wherein at stage B the specific power of a single external mechanical impulse ranks between 0.01 and 0.2 W/mm$^2$, the quick release lasts between 0.1 and 15 ms, and the time taken to achieve maximum impulse is between 1 and 5 ms.

10. The method according to claim 8, wherein the time interval between performing single measurements of a measuring series does not exceed one (1) second and the measurements are performed as many times as necessary for statistical assessment.

* * * * *